(12) United States Patent
Mattern et al.

(10) Patent No.: US 7,172,999 B2
(45) Date of Patent: Feb. 6, 2007

(54) METHOD AND PREPARATIONS FOR STABILIZING BIOLOGICAL MATERIALS BY DRYING METHODS WITHOUT FREEZING

(75) Inventors: Markus Mattern, Heppenheim (DE); Gerhard Winter, Dossenheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/051,918

(22) PCT Filed: Oct. 24, 1996

(86) PCT No.: PCT/EP96/04627

§ 371 (c)(1),
(2), (4) Date: Apr. 27, 1998

(87) PCT Pub. No.: WO97/15288

PCT Pub. Date: May 1, 1997

(65) Prior Publication Data

US 2001/0055617 A1 Dec. 27, 2001

(30) Foreign Application Priority Data

Oct. 25, 1995 (DE) ................. 195 39 574

(51) Int. Cl.
*A61K 38/18* (2006.01)
*C07K 14/505* (2006.01)
(52) U.S. Cl. .................. 514/2; 530/380; 424/489
(58) Field of Classification Search ........ 530/399, 530/380, 412, 427, 417; 514/2, 8; 424/489; 435/69.1, 69.4
See application file for complete search history.

(56) References Cited

U.S. PATENT DOCUMENTS

| | | | |
|---|---|---|---|
| 3,714,353 A * | 1/1973 | Lincoln et al. | 424/243 |
| 3,852,461 A * | 12/1974 | Hester et al. | 424/273 |
| 4,732,889 A * | 3/1988 | Cynshi et al. | 514/8 |
| 4,788,072 A | 11/1988 | Kawamura | |
| 4,806,524 A * | 2/1989 | Kawaguchi et al. | 514/8 |
| 4,992,419 A | 2/1991 | Woog et al. | |
| 5,051,406 A * | 9/1991 | Satoh | 514/21 |
| 5,149,540 A | 9/1992 | Kunihiro et al. | |
| 5,202,117 A | 4/1993 | Tsuji et al. | |
| 5,217,741 A | 6/1993 | Kawachi et al. | |
| 5,290,765 A * | 3/1994 | Wettlaufer et al. | 514/23 |
| 5,354,934 A * | 10/1994 | Pitt et al. | 514/8 |
| 5,356,636 A | 10/1994 | Schneider et al. | |
| 5,376,632 A * | 12/1994 | Konings et al. | 514/8 |
| 5,728,678 A | 3/1998 | Trimbo et al. | |
| 5,763,409 A | 6/1998 | Bayol et al. | |
| 5,919,443 A | 7/1999 | Michaelis et al. | |
| 5,955,448 A * | 9/1999 | Colaco et al. | 514/53 |
| 6,001,800 A * | 12/1999 | Mehta et al. | 514/8 |

| | | |
|---|---|---|
| 2003/0040462 A1 | 2/2003 | Franks et al. |

FOREIGN PATENT DOCUMENTS

| | | |
|---|---|---|
| CA | 2234724 A1 | 4/1997 |
| DE | 3040005 A | 10/1981 |
| EP | 0 106 608 A2 | 4/1984 |
| EP | 0325112 A1 | 7/1989 |
| EP | 0444692 A1 | 9/1991 |
| EP | 0520748 A1 | 12/1992 |
| EP | 0 598 905 A1 | 6/1994 |
| EP | 0 600 730 B1 | 6/1994 |
| EP | 0759939 A4 | 11/1995 |
| EP | 0825885 A4 | 10/1996 |
| EP | 0 682 944 B1 | 6/1998 |
| GB | 2199746 A | 7/1988 |
| JP | 45-38345 | 12/1970 |
| JP | 64-71818 | 3/1989 |
| JP | 1279843 | 11/1989 |
| JP | 2096536 | 4/1990 |
| JP | 2180834 | 7/1990 |
| JP | 3123451 | 5/1991 |

(Continued)

OTHER PUBLICATIONS

Broadhead et al., "The Spray Drying of Pharmaceuticals," Drug Development and Industrial Pharmacy, 18(11 & 12):1169-1206, 1992.

(Continued)

*Primary Examiner*—Anish Gupta
(74) *Attorney, Agent, or Firm*—Rothwell, Figg, Ernst & Manbeck pc

(57) ABSTRACT

The present invention concerns processes for the production of dry, partially amorphous products containing biologically active and in particular therapeutically active material which are macroscopically homogeneous substance mixtures, the substance mixtures being selected from at least one substance of each of the groups
(i) carbohydrate or zwitterion with a polar residue and derivatives thereof, and
(ii) zwitterion with an apolar residue and derivatives thereof, wherein a solution is prepared of the biologically or therapeutically active material and of substances (i) and (ii) and the solution is dried at a product temperature above the freezing point of the solution. In addition the invention concerns new substance mixtures which are obtained by the said process as well as the use thereof in diagnostic or therapeutic methods.

25 Claims, 6 Drawing Sheets

FOREIGN PATENT DOCUMENTS

| | | |
|---|---|---|
| WO | WO 90/12029 A1 | 10/1990 |
| WO | WO 93/19776 A1 | 10/1993 |
| WO | WO 93/23017 A1 | 11/1993 |
| WO | WO 93/23065 A1 | 11/1993 |
| WO | WO 95/24183 A1 | 9/1995 |
| WO | WO 95/31479 A1 | 11/1995 |
| WO | WO 96/18647 A1 | 6/1996 |
| WO | WO 96/32096 A1 | 10/1996 |
| WO | WO 96/32149 A1 | 10/1996 |
| WO | WO 97/14429 A1 | 4/1997 |

OTHER PUBLICATIONS

Alberts et al., *Molecular Biology of the Cell*, Garland Publishing, Inc., New York, p. 92, (1983).

Lehninger, *Biochemistry*, Johns Hopkins University School of Medicine, Worth Publishers, Inc., New York, pp. 259-261 (1972).

\* cited by examiner

Vacuum drying of maltose-L-phenylalanine mixtures
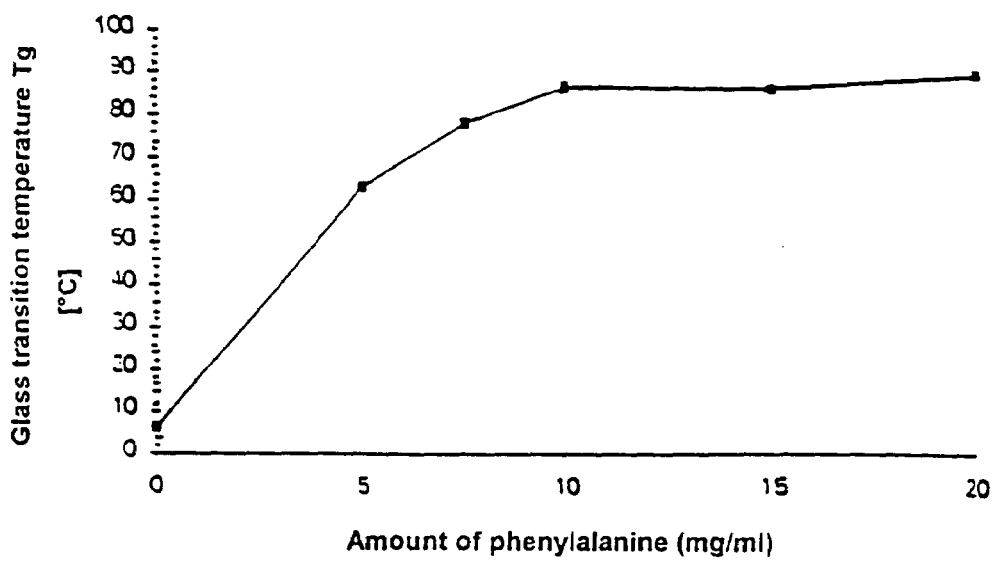
Figure 1 a: Glass transition temperature of individual Maltose-L-Phenylalanine mixtures
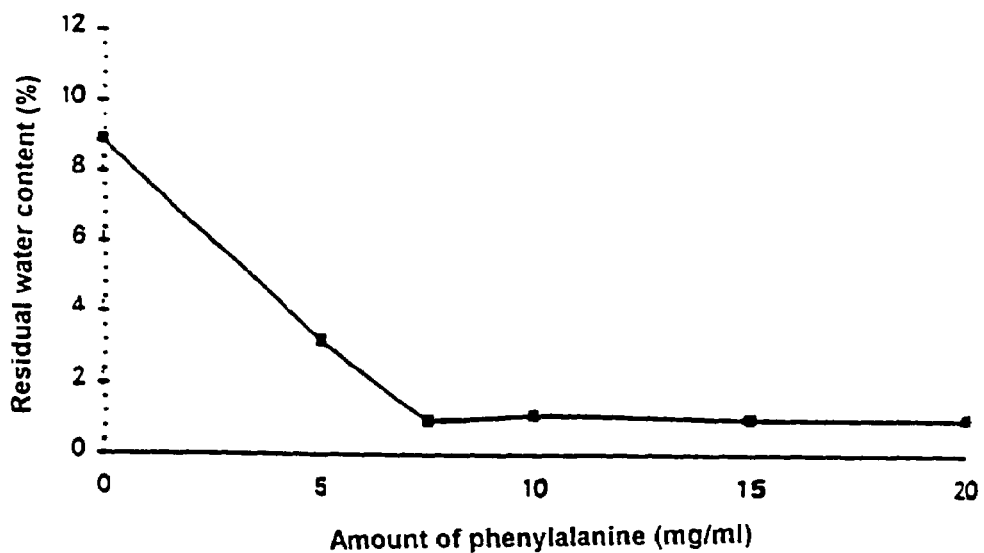
Figure 1 b: Residual water content of individual maltose-L-phenylalanine mixtures Figure 2 a: Phenylalanine 0.12 m vacuum-dried
(crystalline, water content 1.2%)
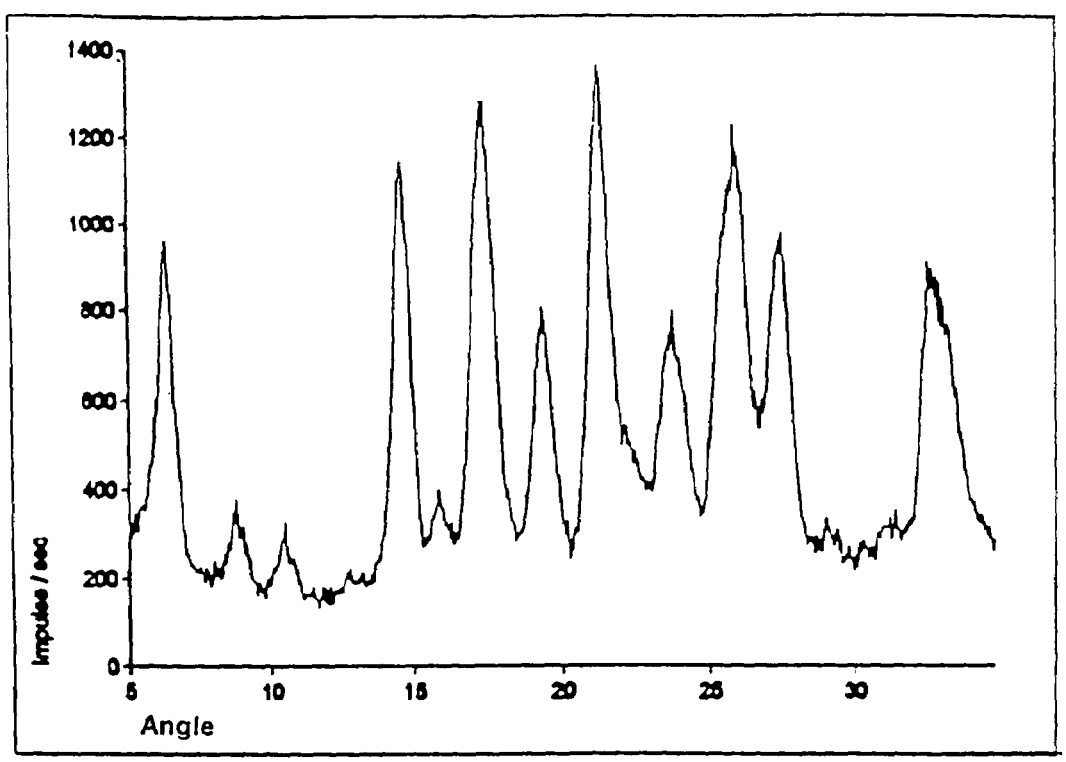

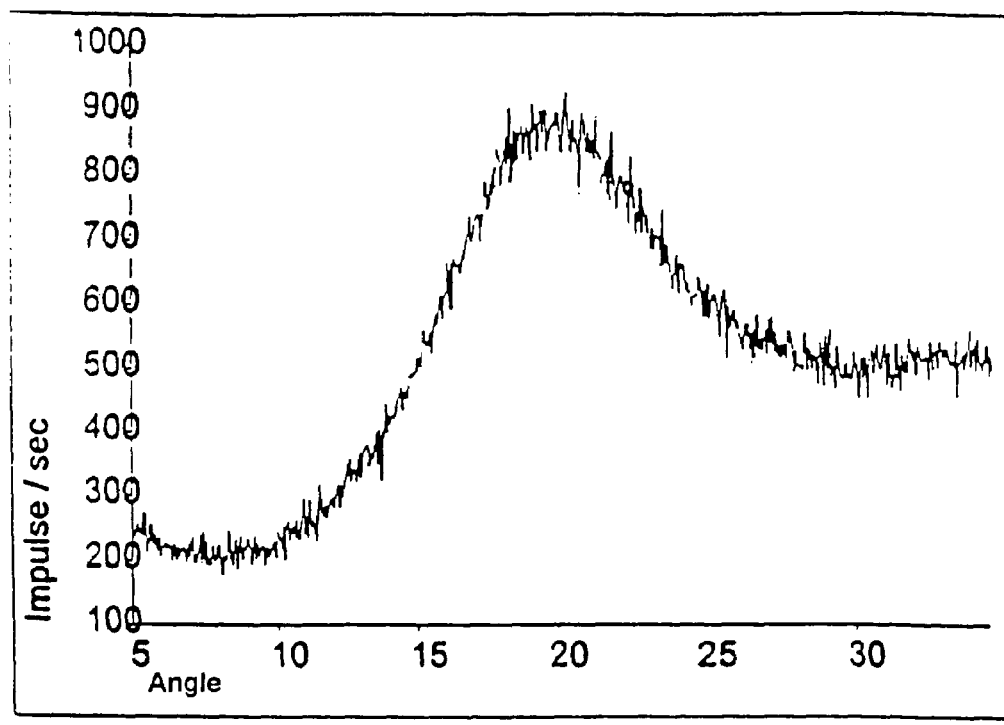
Figure 2 b: Maltose vacuum-dried
(Tg = 50.1°C, water content = 4.0 %)

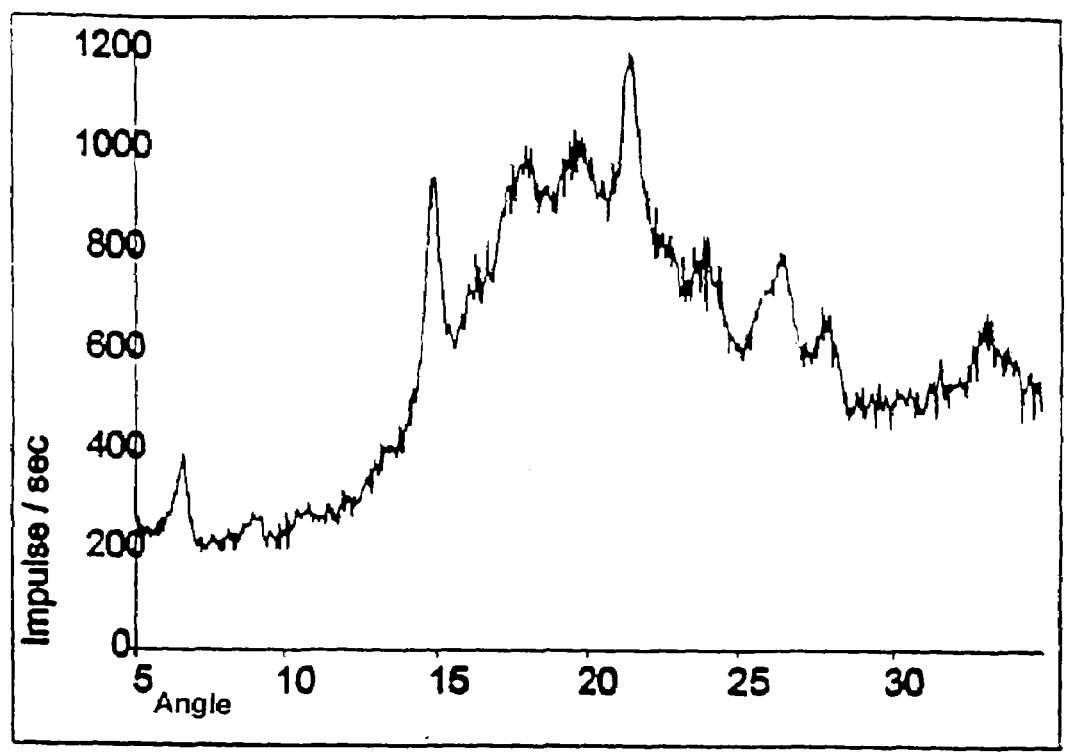
Figure 2 c: Maltose + 10 mg Phenylalanine/ml - vacuum-dried
(Tg = 88°C, water content = 0.7 %)

METHOD AND PREPARATIONS FOR STABILIZING BIOLOGICAL MATERIALS BY DRYING METHODS WITHOUT FREEZING

This application is a national phase application under 35 U.S.C. §371 of International Application No. PCT/EP96/04627 and claims the benefit thereof.

TECHNICAL FIELD

The present invention concerns preparations and processes for stabilizing biological materials by means of drying processes without freezing. Specially selected mixtures of sugars and amino acids and derivatives thereof as well as of various amino acids and derivatives thereof are described which can be used to achieve a particularly advantageous stabilization of peptides, proteins, glycoproteins, antibodies and similar substances after producing dry partially amorphous products by drying processes in which freezing is not employed.

STATE OF THE ART

The production of storage-stable (in particular at room temperature) preparations of biologically active and therapeutic substances such as peptides, proteins, glycoproteins, nucleotides, plasmids, cell fragments, viruses etc. for diagnostic and therapeutic purposes is nowadays of great and continually increasing importance.

Various processes and formulations for producing dry biologically or therapeutically active material have been described. Dry material is understood as substances and mixtures of substances which have a maximum residual moisture of 8% (g/g), preferably of at most 4% (g/g) particularly preferably of at most 2%. Freeze drying processes are widespread but have disadvantages [F. Franks, Cryo Lett. 11, 93–110, (1990); M. J. Pikal, Biopharm. 3 (9), 26–30 (1990); M. Hora, Pharm. Research 8 (3), 285–291 (1992); F. Franks, Jap. J. Freezing Drying 38, 15–16, (1992)]. They consume large amounts of energy, require the use of refrigerants (Frigens) some of which are harmful, and take a long time. For numerous substances, in particular proteins, the step of freezing which is necessary for freeze drying is damaging i.e. destabilizing. This process cannot therefore be used at all for some biological materials.

Alternatives to freeze drying for producing dry protein preparations are processes which dry the material by the application of heat and or a vacuum [F. Franks, R. M. H. Hatley; Stability and Stabilization of Enzymes; Eds. W. J. J. van den Teel, A. Harder, R. M. Butlaar, Elsevier Sci. Publ. 1993, pp. 45–54; B. Roser, Biopharm. 4 (9), 47–53 (1991); J. F. Carpenter, J. H. Crowe, Cryobiol. 25, 459–470 (1988)]. Examples of this are vacuum drying with or without the application of an increased temperature, spray-drying processes in various modifications including the combined application of a vacuum and spraying procedure as well as drum drying and other thin layer drying processes.

Preparations are described in J. F. Carpenter, J. H. Crowe, Biochemistry 28, 3916–3922 (1989); K. Tanaka, T. Taladu, K. Miyajima, Chem. Pharm. Bull. 39 (5), 1091–94 (1991), DE-C-3520228, EP-B-0229810, WO 91/18091, EP-B-0383569, U.S. Pat. No. 5,290,765 which contain sugar or sugar-like substances. In the production of dry sugar preparations the following disadvantages and problems have been found in the processes described in the state of the art: The production of really adequately dry sugar preparations is not possible without the use of a significant amount of energy. This applies particularly to preparations in the final container. It is possible to apply warmth/heat for this but this must be judged to be extremely critical with regard to the stability of the biological materials used. Alternatively in order to achieve adequate drying with a low heat input, drastically increased process times or extremely thin layer thicknesses can be used. Both procedures do not lead to the goal. Long process times are economically extremely unfavourable, moreover the long residence time of an active biological substance in a matrix that is only slowly depleted of water is destabilizing and thus also critical. The drying of thin layer thicknesses does not lead in many cases to an economically viable yield of product i.e. only minimal amounts of product are obtained per unit of time and/or drying area. In addition the processing of biological materials on very large open drying areas can hardly be accomplished with the sterility that is often necessary for the pharmaceutical and diagnostic application.

Drying processes which proceed by means of a vacuum at a temperature that is lower than or slightly above room temperature are milder. However, in many cases it is practically hardly possible to produce dry storage-stable sugar preparations. When sugar solutions are dried increasingly viscous, thick pastes are formed. The residual amount of water or residual moisture remaining in these materials cannot be removed within an economically reasonable period, in many cases the drying comes to a standstill at a high level which is not suitable for stabilization. The degradation manifests itself for example in a decrease in the activity of the stored material, in the formation of aggregation products or by the occurrence of degradation products of a lower molecular weight. A suitable low residual water content for the stabilization of proteins etc. can be identified on the basis of physical parameters. It follows from the literature cited above that preparations suitable for stabilizing proteins etc. should have a glass-like i.e. an amorphous structure the glass transition temperature of which lies above the envisaged storage temperature. The glass transition temperature is that temperature at which an amorphous solid body changes from the glass state into the thick viscous state and vice versa. Drastic changes in viscosity occur in this process and concomitantly in the diffusion coefficients and the kinetic mobility of the proteins and other molecules. Physical parameters such as hardness and modulus change as well as the thermodynamic functions of state: volume, enthalpy and entropy. The glass transition temperature of for example a material containing sugar and its residual water content are linked physically to one another in such a way that increasing amounts of residual water lead to reduced glass transition temperatures and vice versa. Thus the measurement of the glass transition temperature e.g. by differential scanning calorimetry (DSC) can be used to deduce whether a preparation has a suitable residual water content for stabilization and, as described above, whether a drying process is successful or not. In addition to the determination of the glass transition temperature by means of DSC, the presence of amorphous structures can also be proven by means of X-ray diffraction investigations and optical and electron microscopic observations.

Therefore it is desirable to provide a stabilizing matrix for biologically or pharmaceutically active materials with a glass transition temperature that lies above the storage temperature, which contains a low residual moisture and processes for the cost-effective production of such stabilizing matrices.

DESCRIPTION OF THE INVENTION

Surprisingly it was found that the addition of zwitterions with apolar residues to materials containing carbohydrates can change their drying properties in such a positive manner that materials which previously dried poorly and accordingly did not have adequate stabilizing properties could now be dried very rapidly and produced an excellent stability of the biologically and in particular therapeutically active materials formulated therein.

Furthermore it was surprisingly found that carbohydrate-free formulations composed of mixtures of particular zwitterions could also be dried very rapidly and had very good stabilizing properties. In this case a zwitterion with a polar residue must be used together with a zwitterion with an apolar residue. Such zwitterions are preferably aminocarboxylic acids and derivatives thereof and particularly preferably pharmaceutically acceptable amino acids. Zwitterions are understood as low-molecular compounds whose molecular weight is below 10 kDa and preferably below 5 kDa. Processes are described which, without the application of a high temperature i.e. at room temperature, allow preparations according to the invention to be dried in such a way that suitable glass transition temperatures are reached for preparations for stabilizing biologically and in particular therapeutically active substances. Biologically active substances are, in addition to therapeutically active substances, also those which are used in biotechnological processes such as e.g. fermentation. As well as those substances which are used for example in plant protection or as an insecticide. Such biologically and in particular therapeutically active materials can for example be selected from one or several substances of the groups proteins, peptides, glycoproteins, lipoproteins, enzymes, coenzymes, biological membranes, antibodies, antibody fragments, viruses, viral components, vaccines, DNA, RNA, PNA, plasmids, vectors, pheromones, biological therapeutics and diagnostics and derivatives thereof. Biologically active substances are not understood to include foods as such.

The particular advantages of the preparations and processes described here are:

that a freezing is avoided during the drying the drying can be carried out with freeze-drying plants that are already available in the chemical-pharmaceutical industry without any retrofitting filling into commercial containers e.g. glass bottles which is particularly advantageous for an aseptic production can be retained without change process times are of the same order of magnitude as freeze-drying processes and much less toxicologically acceptable auxiliary substances can be used all quantities of energy necessary for freezing can be saved and the use of environmentally harmful refrigerants can be drastically reduced the products obtained are readily visible "cakes" that can be rapidly dissolved again since a partially amorphous state is rapidly attained, the biological material is degraded less than by the processes described in the state of the art.

It should be noted that the particular advantages of the formulations described here of particular mixtures of sugars and amino acids as well as of particular mixtures of at least 2 amino acids are also effective when they are used within the framework of other drying processes which avoid freezing. The accelerated drying effect of the additives as well as the property of the preparations to form amorphous or partially amorphous systems equally applies to spray-drying, drum-drying etc.

An essential feature is that significant amounts of amorphous materials are present as detected by DSC and/or X-ray structural analysis or other suitable methods and that the preparations do not have a completely crystalline character. Crystalline preparations are not suitable for achieving an adequate stability for sensitive biological substances. Completely amorphous preparations are suitable for stabilization and are thus in principle according to the invention but partially amorphous preparations are especially so.

DESCRIPTION OF THE FIGURES

FIG. 1a: glass transition temperatures of individual maltose-L-phenylalanine mixtures FIG. 1b: residual water content of the individual maltose-L-phenylalanine mixtures FIG. 2: powder diffractograms of vacuum-dried
  (a) phenylalanine (water content 1.2%/crystalline),
  (b) maltose (water content 4.0%, Tg=50° C.) and
  (c) phenylalanine and maltose prepared in a manner according to the invention (water content 0.7%, Tg=88° C.).

The diffractograms were recorded with a conventional instrument (Phillips 1730 X-ray) and associated software. The measuring temperature is 25° C., the angular resolution (2θ) 0.05°. Measuring conditions: 1 s per angle at 40 kV tube voltage and 40 mA current strength.

Figure 3:
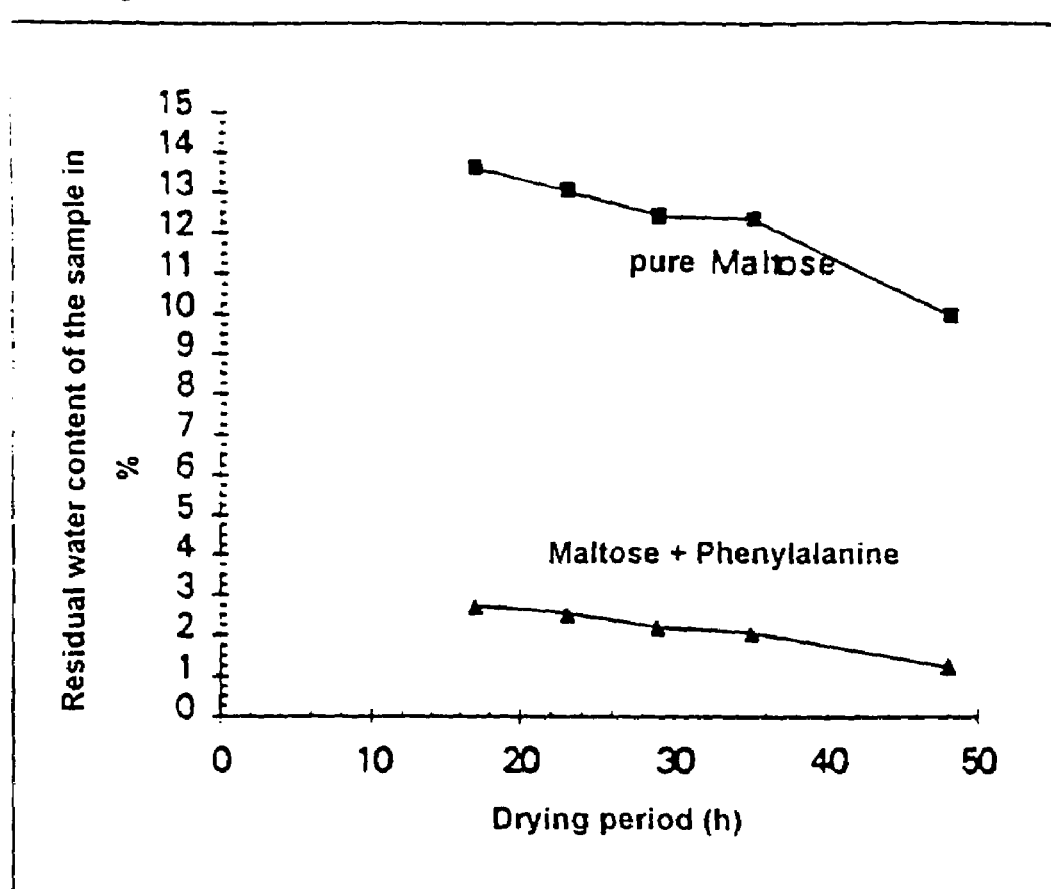
Figure 3:
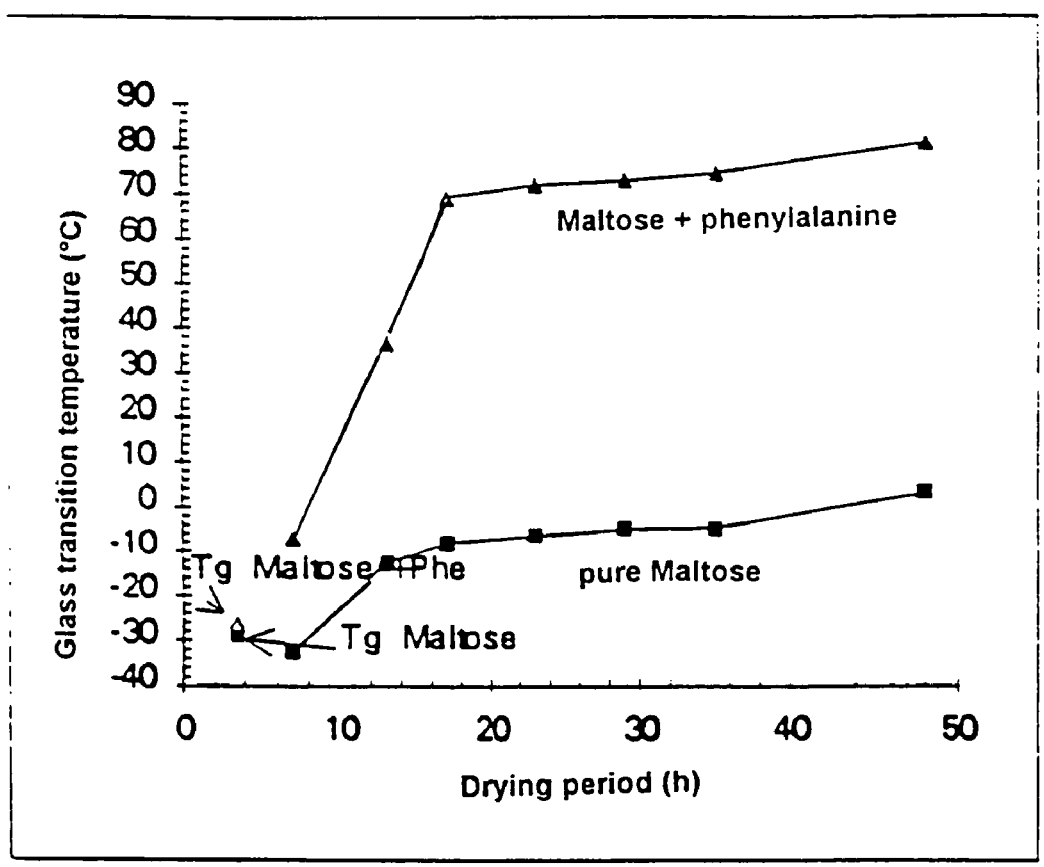

FIG. 3: Time course of the
  (a) residual water content and the
  (b) glass transition temperature of a maltose/phenylalanine preparation according to the invention.

DETAILED DESCRIPTION OF THE INVENTION

The invention is exemplified by 13 examples and 10 comparative examples and is elucidated in the following. In this process formulations and processes were found which drastically improve and accelerate the drying of materials containing sugar by means of vacuum-drying and are suitable for stabilizing relevant therapeutic and diagnostic biological materials. Furthermore completely novel compositions are shown which fulfil the purpose of stabilization while retaining the optimized drying characteristics.

These compositions preferably contain either at least one zwitterion with an apolar residue (e.g. an amino acid such as phenylalanine) and sugar in which the glass transition temperature of the sugar is considerably increased by this addition of zwitterion. Alternatively mixtures of various specially selected amino acids or derivatives thereof can also be used. These mixtures are composed of a zwitterion with an apolar residue and a zwitterion with a polar residue. Sugars can also be added to these mixtures.

As a working hypothesis it was found that in particular mixtures of a sugar or polar zwitterionic substance (e.g. arginine, aspartic acid, glutamic acid, histidine, citrulline, lysine) and an apolar zwitterionic substance (e.g. phenylalanine, isoleucine, methionine, valine, alanine, glycine, tryptophan, cysteine) or derivatives thereof (e.g. acetylphenylalanine ethyl ester) yield the desired results according to the invention. It is easily possible to modify the process and to extend the list of substances described in the examples.

Particularly preferred biologically or therapeutically active materials are antibodies (monoclonal or polyclonal), enzymes and human proteins or human peptides such as e.g. recombinant human erythropoietin (rh-EPO), recombinant human glanulocyte colony stimulating factor (rh-G-CSF) or recombinant plasminogen activator (rPA), nGF, PTH, ularitides, plasmids, viruses, GUP, BP-5.

Preparations free of active substance were used to determine in which manner the addition of amino acids changes the drying of sugar matrices. Example 1 shows that the addition of phenylalanine and arginine to maltose improves its drying properties depending on the added amount of these additives. The specific addition of these auxiliary substances enables the glass transition temperature to be increased by over 65 K and the corresponding residual water content to be easily reduced to below 1% under the same drying conditions. Example 1 shows that the process employed in this case leads to the desired result within 48 hours without any application of heat at all. Maltose without the auxiliary substances added according to the invention has a residual water content of 7–8% under these conditions, the glass transition temperature (Tg) is below room temperature and thus this system is not suitable for stabilizing proteins etc.

The production of preparations according to the invention composed of sucrose and an amino acid from the group of amino acids suitable according to the invention for the production of stabilizing, partially amorphous products is able to avoid certain disadvantages with the formulation containing sucrose while the intrinsic advantages of sucrose can come fully into effect. In comparison to other sugars mentioned in the literature sucrose has a relatively low glass transition temperature at appropriately standardized water contents. Therefore in producing dry preparations containing sucrose it is particularly difficult to attain high Tgs which are substantially above the intended storage temperature. In addition it is difficult to convert sucrose at all into an amorphous form by evaporation drying, the sugar readily crystallizes and thus readily forms a crystalline structure that is unfavourable for stabilizing active biological substances. In addition it can be observed that amorphous sucrose masses relatively rapidly form a large amount of crystals during the course of storage and can completely crystallize after certain storage periods. In this process such a preparation also loses its stabilizing properties. All these problems, risks and deficiencies associated with the use of sucrose can be eliminated by the addition according to the invention of amino acids of the appropriate group. In this connection the use of phenylalanine and arginine (example 2) is particularly preferred. In the comparative example A it is shown that pure sugar masses cannot be dried efficiently even when using longer drying periods. The improved drying effect of amino acids and sugars can be achieved with individual amino acids as well as with amino acid mixtures. Examples 3 and 4 yield corresponding results for this with maltose and sucrose systems. Amino acids have also been found which do not have the improved drying effects e.g. histidine (comparative example B). Example 5 shows that, in addition to amino acids, their structurally related derivatives can also have improved drying effects. The selection of particular amino acids is described in detail but not in a limiting manner or completely comprehensively in example 6. It should be noted that by far not every amino acid leads to the desired effect but only particular amino acids. Also the extent of the effects varies so that particularly preferred combinations or preparations can be mentioned. These are above all phenylalanine, tryptophan, leucine and isoleucine. Furthermore from example 1 and 6 it can be deduced that it is possible to mix amino acids while retaining the improved drying effect. Arginine alone does not have a positive effect but indeed in a mixture with phenylalanine.

The properties of amino acids during vacuum drying was investigated in order to determine whether preparations could also be obtained by means of amino acids which have a glass transition temperature above room temperature in the absence of a sugar matrix. It was surprisingly found that a pure amino acid alone only forms crystalline structures whereas certain amino acid salts and mixtures of amino acids form glass-like matrices (comparative example C and example 7). In order to produce amorphous structures it is necessary to specifically select different amino acids. It was surprisingly found that amino acids can be divided into two groups which apparently have different properties. It is necessary to select at least one amino acid from each group and to produce a corresponding mixture and to dry this. As in the formulation of sugar-amino acid mixtures it is also necessary in this case to have a certain mixing ratio in order to obtain preparations according to the invention (example 7). Then a matrix is obtained with amorphous components which is suitable for stabilizing active biological substances.

The efficacy of the improved drying with regard to the actual goal of stabilizing biologically active material as exemplified for proteins is demonstrated in detail in examples 8–12 and the comparative examples D–J. Examples 8 and 9 together with the comparative examples D–G describe the stabilization of rh-G-CSF, example 10 and comparative example H of erythropoietin and examples 11 and 12 and comparative examples I and J describe the stabilization of lactate dehydrogenase. The surprisingly substantially improved storage stability of the preparations according to the invention compared to vacuum-dried preparations without auxiliary substances and other preparations is exemplified on the basis of storage periods for a protein (rh-G-CSF, example 8 and 9 and comparative examples D, E and F, G), a glycoprotein (rh-EPO, example 10 and comparative example H) and an enzyme (LDH, examples 11, 12 and comparative example I and J). The changes of various rh-G-CSF preparations under storage conditions at various temperatures is shown in the examples. Only preparations according to the invention i.e. partially amorphous glass-like preparations show no significant degradation after six months in the storage temperature range of a few degrees Celsius (refrigerator) up to 40° C. (examples 8 and 9). Corresponding vacuum-dried preparations free of auxiliary substances (comparative example D) show a significant decrease of monomers of up to 20% at room temperature and increased storage temperature (40° C.). Non-amorphous, but rather thick viscous preparations already show significant decreases in their monomer concentration at room temperature after 5 weeks (comparative examples D+E). Crystalline preparations (comparative examples G and J) also show significantly curtailed storage periods. One can see by comparing example 8 and comparative example E that the addition of amino acids to maltose as stabilizers increases the storage period at an increased storage temperature (40° C.) at which less than 10% of the monomers of G-CSF aggregate by more than 10-fold. Comparing example 9 with comparative example G shows that the selection of the amino acids is also decisive for the greatly increased storage period. A comparison of the proportion of monomers in the glycoprotein EPO (example 10, comparative example H) shows that preparations according to the invention at room temperature and increased storage temperature are considerably superior to vacuum-dried EPO without auxiliary substances. A 5-week storage of the sensitive enzyme LDH as preparations according to the invention (examples 11 and 12) compared to vacuum-dried LDH without auxiliary substances (comparative example I) and a crystalline preparation (comparative example J) shows that only preparations according to the invention can be stored at room temperature or higher storage temperatures (30° C.) without a drastic loss in activity. In this connection the additional stabilization of the enzyme by the preparation according to the invention directly after preparation of the samples (activity at 0 weeks>80% compared to 65% with preparations without auxiliary substances and 10% with crystalline preparations) is noteworthy. A typical time course of the drying process of a mixture according to the invention is exemplified in example 13.

In order to produce mixtures according to the invention of at least two amino acids to achieve rapid drying glass-like preparations at least one amino acid and derivatives thereof must be selected from each of the following two groups:

group 1: arginine, aspartic acid, glutamic acid, histidine, citrulline, lysine, ornithine group 2: phenylalanine, isoleucine, leucine, methionine, valine, alanine, glycine, tryptophan, acetylphenylalanine ethyl ester, cysteine, sarcosine.

The sole use of only one amino acid or several amino acids from only one of the two groups does not lead to the advantageous preparations according to the invention. Substance mixtures according to the invention can, as exemplified, be found by admixing various amounts of a zwitterion containing an apolar residue e.g. phenylalanine or derivatives thereof with a solution of a stabilizer of biologically or therapeutically active substances. Subsequently DSC is used to check whether the mixtures dried at room temperature have a glass transition temperature which has been increased by the zwitterionic additive. In this process the glass transition temperature has increased compared to preparations without additives according to the invention by 10K, preferably by 20K and particularly preferably by 40K. The preparations that are advantageous according to the invention are partially amorphous, have a glass transition temperature above 4° C., preferably above 20° C. and particularly preferably above 40° C. and have corresponding residual moisture contents of less than 6%, preferably less than 4%. Their apparent density corresponding to the bulk density is at least 10%, preferably 50% higher than that of the corresponding lyophilisates. They retain their brittle, glass-like, compact, partially amorphous structure for at least 2 weeks, preferably 2 months and particularly preferably 1 year. In addition their drying time (i.e. the time at which the same residual moisture is achieved) is preferably reduced by 25%, particularly preferably halved or even quartered compared to mixtures of substances which contain only one carbohydrate or zwitterion with an apolar residue. These mixtures of substances can also be ground or otherwise processed e.g. used in therapeutic agents or diagnostics in combination with common auxiliary substances and carriers. Therapeutic agents are therapeutic preparations which contain one or several therapeutically active agents in addition to common auxiliary substances and additives. They can be present in the form of tablets, capsules or solid substances from which therapeutically active solutions (e.g. infusion solutions) are prepared by addition of liquid (e.g. sterile water or buffer). In addition they are particularly suitable for administration as a solid substance by means of various processes e.g. as a nasal spray, inhalate or transdermal powder etc.

EXAMPLE 1

Vacuum Drying of Maltose-L-arginine-L-phenylalanine Mixtures

A solution was prepared with a content of 50 mg maltose monohydrate and 0.1 mg polysorbate 80 per ml. Increasing amounts of L-arginine and L-phenylalanine in equal proportions (g/g) were then added to this. The solutions prepared in this manner were sterilized by filtration (0.22 µm cellulose nitrate filter) and then in each case 1 ml solution was filled into 2 ml vials and a freeze-drying stopper was placed on them. The samples prepared in this way were vacuum-dried in the same manner for 48 hours at 20° C. under reduced pressure. After the drying the water content of the samples was determined according to Karl-Fischer and the glass transition temperature was determined by means of differential thermoanalysis (Perkin Elmer DSC7—heating rate of the samples=10 K/min). The measured results show that the addition of certain amounts of the amino acids significantly changes the drying properties of the maltose. Above 7.5 mg of each amino acid the water content of the samples decreases significantly and the glass transition temperature increases correspondingly. At 10 mg each of L-arginine and L-phenylalanine values are achieved which cannot be increased further by further increasing the proportions of amino acid in the dry product. Increasing amounts of amino acids were added to the sugar solution containing 50 mg maltose monohydrate and 0.1 mg polysorbate 80 per ml. The products resulting after drying had the water contents and glass transition temperatures stated here.

TABLE 1

| L-arginine [mg/ml] | L-phenylalanine [mg/ml] | residual water content [%] | glass transition temperature [C.] |
| --- | --- | --- | --- |
| 0 | 0 | 7.68 | 12.86 |
| 1 | 1 | 7.95 | 12.47 |
| 2.5 | 2.5 | 7.71 | 12.91 |
| 5 | 5 | 7.75 | 13.67 |
| 7.5 | 7.5 | 3.55 | 52.04 |
| 10 | 10 | 0.54 | 80.57 |
| 12.5 | 12.5 | 0.76 | 73.14 |

EXAMPLE 2

Vacuum Drying of Sucrose-L-arginine-L-phenylalanine Mixtures

Increasing amounts of L-arginine and L-phenylalanine in equal proportions (g/g) were added to a sucrose solution which contained 50 mg sucrose and 0.1 mg polysorbate 80 per ml. The samples were prepared as in example 1, dried and analysed. With amounts of up to 10 mg of each amino acid completely crystalline products were obtained. Partially amorphous products with a glass transition could only be identified above 10 mg L-arginine and 10 mg L-phenylalanine per ml. In this example not only the drying property of a solution was improved by addition of amino acids but the system was converted into a partially amorphous state by this addition. Increasing amounts of amino acids were added to a sugar solution containing 50 mg sucrose and 0.1 mg polysorbate 80 per ml. The products resulting after drying had the water contents and glass transition temperatures stated here.

TABLE 2

| L-arginine [mg/ml] | L-phenylalanine [mg/ml] | residual water content [%] | glass transition temperature [C.] |
|---|---|---|---|
| 0 | 0 | 2.97 | crystalline |
| 1 | 1 | 1.11 | crystalline |
| 2.5 | 2.5 | 3.46 | crystalline |
| 5 | 5 | 6.11 | crystalline |
| 10 | 10 | 3.43 | 18.56 |
| 15 | 15 | 1.53 | 53.70 |
| 20 | 20 | 1.60 | 58.78 |

COMPARATIVE EXAMPLE A

Vacuum Drying of Pure Sugar Solutions

A maltose monohydrate and a sucrose solution with a concentration of 50 mg/ml were prepared. These sugar solutions were then filtered, filled and analysed as described in example 1. It could be shown that even when dried for 72 hours at 50° C. under reduced pressure it is not possible to dry 50 mg sugar in a 2 ml vial to a satisfactory residual moisture content so that the glass transition lies above 25° C. The maltose product had a viscous consistency and had a residual water content of 6.4%. The glass transition was at 20° C. In the case of sucrose 6.0% residual water was still present, the glass transition was at 14° C. As a comparison the pure sugar solutions were also dried for 48 hours at 20° C. under reduced pressure. The resulting products were even more moist and the glass transition was therefore even lower than the samples dried at 50° C. This experiment clearly shows that only by the addition of certain amino acids is it possible to dry sugar layers in injection bottles or similar containers to low residual moisture contents by means of vacuum drying. Thus the improvement in the drying properties by the addition of amino acids is made clear.

TABLE 3

| drying | maltose residual water content | glass transition temperature | sucrose residual water content | glass transition temperature |
|---|---|---|---|---|
| 72 h at 50° C. | 6.4% | 20.0° C. | 6.0% | 14.0° C. |
| 48 h at 20° C. | 8.9% | 6.1° C. | 9.3% | −1.8° C. |

EXAMPLE 3

Vacuum Drying of Maltose-L-phenylalanine and Maltose-L-isoleucine Mixtures

In this experiment binary mixtures of amino acids and maltose monohydrate were prepared. It is intended to examine whether the amino acids used in this case have the property to improve drying and how the improved drying effect depends on the quantity of the individual amino acids. Increasing amounts of L-phenylalanine or L-isoleucine were added to a solution which contained 50 mg maltose monohydrate per ml. The solutions prepared in this way were sterilized by filtration (0.22 μm cellulose nitrate filter) and then 1 ml of the solution in each case was filled into 2 ml vials and capped with freeze drying stoppers. The samples prepared in this manner were vacuum-dried for 48 hours at 20° C. under reduced pressure. After drying the water content of each of the samples was determined in quadruplicate according to Karl-Fischer and the glass transition temperature was determined by means of differential thermoanalysis (Perkin Elmer DSC7—heating rate of the samples=10 K/min) of two samples of each mixture.

a. Result Maltose-L-phenylalanine

The measured results clearly show the positive influence of L-phenylalanine on the drying properties of maltose. Already small amounts of L-phenylalanine are adequate to increase the glass transition temperature of a sugar glass under constant drying conditions by ca. 50° C. (FIGS. 1a and 1b). The improved drying effect reaches a maximum at 10 mg/ml L-phenylalanine. No further improvement can be achieved by adding larger amounts of L-phenylalanine. Thus the addition of L-phenylalanine increased the glass transition temperature by ca. 80° C. compared to pure maltose. With large amounts of L-phenylalanine (10–20 mg/ml) no differences with regard to the drying properties were discernible in this experiment. This, however, changes with shortened drying periods. In this case an increase in the glass transitions can also be seen with increasing amounts of L-phenylalanine in the range 10–20 mg per ml. Table 4 shows the amount of L-phenylalanine in the sugar solution and the resulting residual water content and glass transition temperature Tg.

TABLE 4

| L-phenylalanine [mg/ml] | residual water content [%] | glass transition temperature [° C.] |
|---|---|---|
| 0 | 8.91 | 6.1 |
| 5 | 3.21 | 62.8 |
| 7.5 | 0.95 | 77.7 |
| 10 | 1.12 | 86.0 |
| 15 | 0.99 | 85.2 |
| 20 | 0.99 | 88.2 |

In addition powder diffractograms of vacuum-dried phenylalanine, maltose and a mixture according to the invention of phenylalanine and maltose were recorded (FIGS. 2a, 2b, 2c). Pure phenylalanine shows a typical diffractogram of a crystalline substance (FIG. 2a) whereas maltose shows a diffractogram of an amorphous substance (FIG. 2b). Only in the case of the mixture according to the invention are partially amorphous structures formed that are recognizable as the discrete diffraction maxima on a broad background signal (FIG. 2c).

b. Result Maltose-L-isoleucine

Various amounts of L-isoleucine were added to a stock solution containing 50 mg maltose monohydrate per ml and the individual mixtures were dried at 20° C. An improved drying effect with an increasing amount of amino acid is clearly apparent. The addition of 20 mg/ml L-isoleucine (mixing ratio 5:2 by weight) increases the Tg of the maltose product by ca. 20° C. Table 5 shows the amount of L-isoleucine in the sugar solution and the resulting residual water content and the glass transition temperature Tg.

TABLE 5

| isoleucine [mg/ml] | residual water content [%] | glass transition temperature [° C.] |
|---|---|---|
| 0 | 8.91 | 6.1 |
| 5 | 7.84 | 13.7 |
| 10 | 7.52 | 17.7 |
| 15 | 6.77 | 19.4 |
| 20 | 5.34 | 24.7 |

EXAMPLE 4

Vacuum Drying of Sucrose-L-leucine

Binary mixtures of sucrose containing various amino acids were prepared in the following experiments. The aim was to check whether the amino acids used have an improved drying effect on sucrose. Increasing amounts of L-leucine were added to a solution that contained 50 mg sucrose per ml. The solutions were treated as described in example 3.

Result Sucrose-L-leucine

Sucrose forms a crystalline product with small amounts of L-leucine. This formation of crystals could also be observed in example 2 with L-arginine and L-phenylalanine. Thus sucrose forms crystalline products when it is mixed with certain amino acids. The pure sugar and mixtures with larger proportions of L-leucine form systems with a glass transition. This means that a partially amorphous structure is present. This means that only concentrations of L-leucine above 15 mg/ml improve the drying properties of pure sucrose and that the glass transition can be increased by addition of this amino acid by ca. 18° C. L-leucine is therefore an amino acid with an improved drying effect. Table 6 shows the amount of L-leucine in the sugar solution and the resulting residual water content and glass transition temperature Tg of the final products.

TABLE 6

| L-leucine [mg/ml] | residual water content [%] | glass transition temperature [° C.] |
|---|---|---|
| 0 | 9.34 | −1.8 |
| 5 | 6.23 | crystalline |
| 10 | 6.50 | crystalline |
| 15 | 5.81 | 16.4 |
| 20 | 5.02 | 16.1 |

COMPARATIVE EXAMPLE B

Vacuum Drying of Sucrose-L-histidine Mixtures

The experiments were carried out as described in example 4. L-histidine was used instead of L-leucine. The mixture sucrose-L-histidine forms amorphous products when dried in a vacuum in which no improved drying effect is observed. The structures dry poorly independently of the mixing ratio and the residual water contents and glass transitions of the mixtures are of the same order of magnitude as the results of the pure sugar. Consequently L-histidine has no improved drying effect. Table 7 shows the amount of L-histidine in the sugar solution and the resulting residual water content and glass transition temperature Tg of the final products.

TABLE 7

| L-histidine [mg/ml] | residual water content [%] | glass transition temperature [° C.] |
|---|---|---|
| 0 | 9.34 | −1.8 |
| 5 | 11.23 | −1.4 |
| 20 | 9.78 | −2.6 |

EXAMPLE 5

Vacuum Drying of Sucrose-L-tryptophan and Sucrose-N-acetyl-L-phenylalanine Ethyl Ester (APE) Mixtures A solution containing 10 mg L-tryptophan per ml and a solution containing 3 mg APE per ml were prepared in this experiment (APE only has a limited solubility in water). Sucrose was added in increasing amounts to both solutions. The solutions obtained in this way were treated and dried as described in example 3. A sucrose solution (50 mg/ml) was dried under the same drying conditions as a comparison in this experiment. This had a residual water content of 9.98% and a glass transition of −6.25° C. in the final product.

a. Table 8 shows the amount of sucrose in the L-tryptophan solution (10 mg/ml) and the resulting residual water content and glass transition temperature of the final products.

TABLE 8

| Sucrose [mg/ml] | residual water content [%] | glass transition temperature [° C.] |
|---|---|---|
| 20 | 3.09 | 37.30 |
| 40 | 4.19 | 22.51 |
| 60 | 5.37 | 14.44 | b. Table 9 shows the amount of sucrose in the APE solution (3 mg/ml) and the resulting residual water content and glass transition temperature of the final products.

TABLE 9

| Sucrose [mg/ml] | residual water content [%] | glass transition temperature [° C.] |
|---|---|---|
| 10 | 6.15 | 13.3 |
| 40 | 8.33 | 1.4 |

The results show that both substances examined, L-tryptophan and APE, exhibit an improved drying effect. The glass transition temperature of the partially amorphous product can be increased by ca. 45° C. with constant drying conditions using L-tryptophan. It is possible to increase the glass transition temperature by 20° C. with constant drying conditions using APE.

EXAMPLE 6

Vacuum Drying of Other Sugar-amino Acid Mixtures

Binary mixtures of maltose monohydrate or sucrose were prepared with one L-amino acid in this experiment. In this case amino acids were added to the sugar solution at weight ratios of sugar to amino acid of 5:2 to 1:1. The aim was to check whether the respective amino acid exhibited an improved drying effect with the corresponding sugars. The solutions were prepared, treated and dried as described in example 4. In detail these were the following mixtures:

a. Mixtures containing maltose monohydrate

TABLE 10

| Amino acid used | Amount of AA [mg/ml] | Amount of sugar [mg/ml] | Residual water content [%] | Glass transition [° C.] |
|---|---|---|---|---|
| — | — | 50 | 8.91 | 6.1 |
| L-arginine | 10 | 50 | 8.10 | 10.3 |
| L-arginine | 20 | 50 | 8.63 | 7.1 |
| L-leucine | 20 | 50 | 5.42 | 20.9 |
| L-leucine | 20 | 20 | 1.87 | 56.05 |
| L-histidine | 20 | 50 | 9.78 | 5.3 |
| L-isoleucine | 20 | 20 | 3.12 | 37.9 |
| L-methionine | 15 | 30 | 7.45 | 9.7 |
| L-methionine | 20 | 20 | 2.70 | 34.4 |
| L-valine | 20 | 20 | 4.93 | 18.8 | b. Mixtures containing sucrose

TABLE 11

| amino acid used | amount of AA [mg/ml] | amount of sugar [mg/ml] | residual water content [%] | glass transition [° C.] |
|---|---|---|---|---|
| — | — | 50 | 9.34 | −1.8 |
| L-alanine | 15 | 30 | 6.04 | 2.8 |
| L-alanine | 20 | 20 | 4.46 | 11.7 |
| L-glycine | 20 | 20 | 4.47 | 5.3 |
| L-phenylalanine | 20 | 50 | 1.12 | 62.7 |
| L-serine | 15 | 30 | 11.77 | −15.1 |
| L-serine | 20 | 20 | 10.61 | −14.4 |

The results of the drying show that L-histidine has no positive influence on the drying properties of sugars (Table 10). L-serine even worsens the drying of sugars further (Table 11). L-leucine, L-isoleucine and L-methionine have an improved drying effect (Table 10). This becomes clear when increasing amounts of these amino acids are added to the sugar solution. L-valine and L-alanine are found only to improve drying when there are large amounts of amino acid in the product; L-arginine and L-glycine have a weakly positive influence. The very good effect of L-phenylalanine on the drying behaviour is also apparent in binary mixtures with sucrose (Table 11). The product dries well and has a very high glass transition.

COMPARATIVE EXAMPLE C

Vacuum Drying of Amino Acid Solutions or of Solutions of Amino Acid Salts

Solutions were prepared of individual amino acids or salts of individual amino acids and sterilized by filtration (0.22 μm cellulose nitrate filter). 1 ml of each solution was dispensed into 2 ml vials and capped with freeze-drying stoppers. The samples prepared in this manner were vacuum-dried for 48 hours at 20° C. under reduced pressure. After drying the water content of the samples was determined according to Karl-Fischer and the glass transition temperature was determined by means of differential thermoanalysis (Perkin Elmer DSC7—heating rate of the samples=10 K/min). The following solutions were dried and the stated residual water contents and DSC measuring results were obtained:

a. Amino acids

TABLE 12

| amino acid | concentration [mol/l] | [mg/ml] | residual water content [%] | DSC measuring result [° C.] |
|---|---|---|---|---|
| L-alanine | 0.24 | 21.38 | 0.81 | crystalline |
| L-arginine | 0.24 | 41.80 | 0.52 | crystalline |
| L-citrulline | 0.24 | 42.05 | 4.9 | crystalline |
| L-cysteine | 0.24 | 29.08 | 2.61 | crystalline |
| glycine | 0.24 | 18.02 | 0.76 | crystalline |
| L-histidine | 0.12 | 18.62 | 0.77 | crystalline |
| L-isoleucine | 0.12 | 15.74 | 1.10 | crystalline |
| L-leucine | 0.12 | 15.74 | 1.62 | crystalline |
| L-lysine | 0.24 | 35.09 | 0.79 | crystalline |
| L-methionine | 0.12 | 17.91 | 1.57 | crystalline |
| L-phenylalanine | 0.12 | 19.82 | 1.53 | crystalline |
| L-proline | 0.24 | 27.63 | 19.93 | crystalline |
| L-serine | 0.24 | 25.22 | 0.44 | crystalline |
| L-threonine | 0.24 | 28.59 | 0.45 | crystalline |
| L-valine | 0.24 | 28.12 | 0.57 | crystalline | b. Salts of amino acids

TABLE 13

| amino acid | concentration [mol/l] | [mg/ml] | pH value | residual water content [%] | DSC measuring result [° C.] |
|---|---|---|---|---|---|
| L-arginine HCl | 0.25 0.30 | 43.55 10.93 | 2.70 | 6.46 | 3.51 |
| L-arginine H$_3$PO$_4$ | 0.25 0.15 | 43.55 14.70 | 6.81 | 3.3 | 5.17 |
| L-arginine H$_2$SO$_4$ | 0.25 0.15 | 43.55 14.71 | 2.89 | 3.24 | 6.67 |
| L-arginine HNO$_3$ | 0.25 0.30 | 43.55 18.90 | 2.58 | 2.66 | crystalline |
| L-arginine acetic acid | 0.25 0.30 | 43.55 18.0 | 5.24 | 11.04 | crystalline |
| L-aspartic acid NaOH | 0.12 0.12 | 15.97 4.8 | 4.97 | 9.65 | 27.7 |
| L-glutamic acid NaOH | 0.12 0.12 | 17.66 4.8 | 5.14 | 14.69 | 5.5 |
| L-ornithine HCl | 0.24 | 40.47 | 5.39 | 0.4 | crystalline |

The result shows that amino acids are present in a crystalline form after vacuum drying. Only salts of basic and acidic amino acids form amorphous structures during these drying conditions which, however, dry extremely poorly and their glass transition temperature lies below room temperature under the selected conditions.

EXAMPLE 7

Vacuum Drying of L-arginine-L-phenylalanine Mixtures and an L-arginine-L-isoleucine Mixture In this experiment various mixtures of L-arginine and L-phenylalanine were prepared, treated, dried and examined as in comparative example C. Specifically the following binary mixtures were prepared and dried:

TABLE 14

| molar mixing ratio | L-arginine [mol/l] | L-arginine [mg/ml] | L-phenylalanine [mol/l] | L-phenylalanine [mg/ml] | residual water content [%] | glass transition temperature [° C.] |
|---|---|---|---|---|---|---|
| 1:1 | 0.12  | 20.90 | 0.12  | 19.82 | 2.27  | 59.5  |
| 2:1 | 0.16  | 27.87 | 0.08  | 13.21 | 9.32  | 1.7   |
| 3:1 | 0.18  | 31.35 | 0.06  | 9.91  | 9.40  | 2.8   |
| 4:1 | 0.192 | 33.44 | 0.048 | 7.928 | 9.96  | 1.3   |
| 5:1 | 0.20  | 34.83 | 0.04  | 6.61  | 10.73 | 0.0   |
| 6:1 | 0.206 | 35.88 | 0.034 | 5.61  | 10.03 | 1.3   |
| 7:1 | 0.21  | 36.58 | 0.03  | 4.96  | 11.38 | 1.0   |
| 1:2 | 0.06  | 10.45 | 0.12  | 19.82 | 2.85  | 47.2  |
| 1:3 | 0.04  | 6.97  | 0.12  | 19.82 | 3.43  | 46.2  |
| 1:4 | 0.03  | 5.23  | 0.12  | 19.82 | 3.66  | 43.45 |

This experiment shows that by mixing two amino acids which if dried alone would result in crystalline products it is possible to produce partially amorphous structures. In the selected mixing ratios these dry so well that partially amorphous structures with a high glass transition temperature and a low residual water content result.

It is interesting that there is an optimal mixing ratio with the highest glass transition. Within this experiment a further solution was prepared which contained 0.15 mol/l L-arginine and L-isoleucine.

TABLE 15

| molar mixing ratio | L-arginine [mol/l] | L-arginine [mg/ml] | L-isoleucine [mol/l] | L-isoleucine [mg/ml] | residual water content [%] | glass transition temperature [° C.] |
|---|---|---|---|---|---|---|
| 1:1 | 0.15 | 26.13 | 0.15 | 19.68 | 1.05 | 53.27 |

In this case a product resulted with a glass transition of 53.27° C. and 1.05% residual water content. By mixing two amino acids it was possible to construct a partially amorphous structure which can be readily dried; the glass transition temperature was increased by ca. 50° C. compared to arginine salts of mineral acids (comparative example C).

EXAMPLE 8 rh-G-CSF Vacuum-dried in a Maltose Formulation Containing L-arginine and L-phenylalanine A solution containing 50 mg maltose, 10 mg L-phenylalanine and 10 mg L-arginine per ml was prepared. In addition this solution contained 0.1 mg polysorbate 80 and 0.35 mg rh-G-CSF per ml. The pH value of the formulation was adjusted to pH 7.4 with hydrochloric acid. The proteinaceous solution was prepared under aseptic conditions and sterilized by filtration (polyvinylidene difluoride filter 0.22 μm). Then in each case 1 ml of the solution was dispensed into 2 ml vials. The filled vials provided with freeze drying stoppers were then dried isothermally for 48 hours at 20° C. under reduced pressure. A dry product resulted with a residual water content of 1.16% and a glass transition temperature of 75° C. The samples prepared in this manner were stored at various temperatures and the protein stability was assessed after various storage periods.

In the case of rh-G-CSF the proportion of dimer that has formed in the manufactured product is a good criterium for assessing the stability of the product. Therefore the amounts of monomer and dimer determined by means of exclusion chromatography (4 single measurements per condition) are a measure for the stabilizing action of our preparations produced by drying. In exclusion chromatography protein molecules are separated in a dissolved state according to their particle size i.e. high molecular components (dimers) are separated from rh-G-CSF monomers. The examination (HP-SEC) was carried out on a HPLC system from Shimadzu using a coolable autosampler (Waters TM 717). A TSK gel G2000 SW (7.5×300) column from the TosoHaas company was used as the separating column. The separated components were detected photometrically at 214 nm (Shimadzu photometer LC-GA). A 0.1 m sodium-potassium phosphate buffer pH 6.2 was used as the mobile solvent which was applied at a flow rate of 0.6 ml/min at room temperature. The samples to be examined were dissolved with redistilled water in such a way that the initial concentration was again prepared (addition of 1 ml). These dissolved samples were then stored in the autosampler cooled to 6° C. until examination. The amount of injected sample was 20 μl (=7 μg G-CSF), the running time of the sample was 32 min. The results were evaluated using the G-CSF working standard. In order to additionally qualitatively evaluate the products, SDS gel electrophoresis with silver staining was carried out additionally for each quantity determination. The results of the SDS gel electrophoresis are shown in example 8b FIG. 9. In aqueous solutions the protein denatures completely within a few hours at temperatures between 45° C. and 47° C. With this formulation it was possible to stabilize the protein for weeks even at a storage temperature of 50° C.

a. Stability of rh-G-CSF in a vacuum-dried maltose formulation containing L-arginine and L-phenylalanine.

TABLE 16

| Storage period [weeks] | Monomer contents obtained in a HP-SEC are stated in % | | | | |
|---|---|---|---|---|---|
| | Storage temperature | | | | |
| | KS | RT | 30° C. | 40° C. | 50° C. |
| 0  | —      | 99.83% | —      | —      | —      |
| 5  | 99.94% | 99.93% | 99.86% | 99.89% | 99.87% |
| 13 | 99.83% | 99.86% | 99.88% | 99.83% | 99.83% |
| 26 | 99.76% | 99.75% | 99.55% | 99.36% | 99.21% |
| 39 | 99.68% | 96.73% | 96.40% | 93.81% | 89.27% |
| 52 | 98.34% | 94.81% | 94.70% | 91.27% | 86.27% |

KS = refrigerator temperature = 4–6° C.
RT = room temperature = 20–22° C.

The results of the exclusion chromatography clearly show that this formulation enables the stabilization of the protein rh-G-CSF over a longer time period in such a vacuum-dried preparation. The experiment shows that it is possible to stabilize rh-G-CSF below the glass transition temperature in a vacuum-dried, partially amorphous maltose formulation containing L-arginine and L-phenylalanine.

b. Review of the results of the SDS gel electrophoresis of all formulations which contained the active substance rh-G-CSF.

Firstly polyacrylamide gels containing SDS were prepared the separating gel of which contained 15% acrylamide and the collecting gel of which contained 3% acrylamide and 1% sodium dodecylsulfate (SDS). The preparation of the samples was such that 1 mixed sample was prepared from 3 injection bottles. Subsequently this sample solution was diluted with a sample buffer containing dithithreitol (DTT) and bromophenol blue so that an rh-G-CSF concentration of 150 µg/ml resulted. The samples were denatured for 5 min at 95° C. in a pre-heated heating block. The proteins "Combithek calibration proteins for chromatography MW 18000–300000" from Boehringer Mannheim were used as calibration proteins. These were prepared and treated exactly as the rh-G-CSF samples. In addition an rh-G-CSF working standard was prepared which was used as a comparison. The gel electrophoresis was carried out by means of a Midget gel electrophoresis unit (Pharmacia-LKB 2050) and an accompanying voltage instrument. After the electrophoresis buffer had been filled, 20 µl sample (i.e. 3 µg rh-G-CSF) was filled into each gel pocket. After closing the gel electrophoresis chamber and turning on the water cooling a voltage of 80 V was applied which was increased to 130 V after the collecting gel was passed. Shortly before the bromophenol blue band reached the end of the gel the electrophoresis was ended. The gels were removed from the chamber and washed briefly with redistilled water. Then a silver staining was carried out according to the accompanying instructions using a Daiichi 2D silver stain II kit. After the staining was completed the gels were evaluated optically.

TABLE 17

Results of the gel electrophoresis

| Lane | Preparation | Visual result |
|---|---|---|
| 1 | calibration proteins | |
| 2 | example 8: maltose formulation containing L-arginine and L-phenylalanine | only monomers |
| 3 | comparative example D: drying without auxiliary substances | monomers and dimers |
| 4 | comparative example E: pure maltose formulation | monomers, dimers and trimers |
| 5 | calibration proteins | |
| 6 | example 9: sugar-free formulation containing L-arginine and L-phenylalanine | only monomers |
| 7 | comparative example F: L-arginine formulation containing phosphoric acid | monomers and dimers |
| 8 | comparative example G: crystalline L-valine-L-glycine formulation | monomers, dimers and degradation products |

In this investigation the formulations of examples 8 and 9 only show monomers. In the comparative examples D and F dimers are also present in addition to the monomer, and in example E trimers are additionally detected. In the crystalline L-valine-L-glycine preparation of comparative example G one also sees two degradation products whose molecular mass is smaller than that of the monomer and 2 weak bands of degradation products whose molecular mass lies between that of the monomer and the dimer.

This sensitive method enables degradation and aggregation products of the monomer which were present in amounts of >1% to be visualized very well.

COMPARATIVE EXAMPLE D

Vacuum Drying of rh-G-CSF Without Addition of Auxiliary Substances

In this experiment a solution was prepared which only contained the protein rh-G-CSF at a concentration of 0.35 mg/ml in a dilute phosphate buffer (ca. 0.01 m). This protein solution was prepared, treated and analysed as described in example 8. In this preparation it was not possible for technical reasons to determine the residual water content and glass transition temperature of the final products. Stability data for vacuum-dried rh-G-CSF without auxiliary substances.

TABLE 18

The amounts of monomer obtained in the HP-SEC are stated in %

| Storage period [weeks] | Storage temperature | | |
|---|---|---|---|
| | KS | RT | 40° C. |
| 0 | — | 97.84% | — |
| 5 | 94.90% | 94.53% | 93.96% |
| 13 | 91.31% | 89.66% | 78.23% |
| 26 | 80.06% | 73.60% | 52.22% |

KS = refrigerator temperature = 4–6° C.
RT = room temperature = 20–22° C.

The stability data for the pure protein show very clearly the stabilizing effect of the auxiliary substances of the formulation described in example 8. Also in the case of this formulation SDS gel electrophoresis with silver staining was carried out in each investigation. See example 8 b for the results.

COMPARATIVE EXAMPLE E rh-G-CSF Vacuum-dried in a Pure Maltose Formulation

A solution containing 50 mg maltose monohydrate, 0.1 mg polysorbate 80 and 0.35 mg rh-G-CSF per ml was prepared. The pH value of the formulation was adjusted to 7.4 using sodium hydroxide solution. The starting solution and the final products were prepared, treated and analysed as described in example 8. As has already been shown in example 1 it is difficult to dry maltose within 48 hours to a low residual moisture content without addition of amino acids. Therefore products are formed with a residual water content of 10.43% and a glass transition temperature of −2° C. At the storage temperatures, i.e. above the glass transition, no amorphous brittle glass was present but instead a highly viscous, glutinous mass. Stability of rh-G-CSF in a vacuum-dried maltose preparation without amino acids.

TABLE 19

The amounts of monomer obtained in the HP-SEC are stated in %

| Storage period [weeks] | Storage temperature | | | | |
|---|---|---|---|---|---|
| | KS | RT | 30° C. | 40° C. | 50° C. |
| 0 | — | 97.99% | — | — | — |
| 5 | 98.26% | 96.82% | 93.91% | 67.45% | 42.63% |
| 13 | 97.15% | 90.49% | 73.70% | 30.05% | 18.52% |
| 26 | 97.05% | 88.23% | 71.32% | 22.30% | 15.27% |

For the results of the SDS gel electrophoresis see example 8b. The result shows that it is not advantageous to store rh-G-CSF in a sugar mass without amino acids. The stability is significantly lower than in a vacuum-dried bulk (comparative example D) and in an optimized vacuum-dried formulation (example 8). This experiment clearly shows the necessity of adding amino acids to sugars when vacuum drying in order to obtain products with high glass transitions in which the protein is then stabilized by the amorphous supporting structure of auxiliary agent. Storing the products below the glass transition temperature proves to be necessary for the stabilization of the active substance. It should also be noted that maltose had completely crystallized after 4 weeks in those samples that had been stored at 40 and 50° C. Such physical changes in the samples during storage should be avoided; they accelerate the decrease in the monomer content.

EXAMPLE 9 rh-G-CSF in a Vacuum-dried Sugar-free L-arginine-L-phenylalanine Formulation

A solution containing 20 mg L-arginine and 20 mg L-phenylalanine, 0.1 mg polysorbate 80 and 0.35 mg rh-G-CSF per ml was prepared. After the pH value had been adjusted to pH 7.4 with hydrochloric acid, the solution was treated, dried and analysed as described in example 8. After the drying was completed, a homogeneous product was present with a glass transition temperature of 77.0° C. and a residual water content of 1.30%. Stability of rh-G-CSF in a vacuum-dried arginine-phenylalanine formulation.

TABLE 20

The amounts of monomer obtained in the HP-SEC are stated

| Storage period [weeks] | Storage temperatures | | | | | |
|---|---|---|---|---|---|---|
| | KS | RT | 30° C. | 40° C. | 60° C. | 80° C. |
| 0 | — | 99.57% | — | — | — | — |
| 4 | 99.36% | 99.36% | 99.50% | 99.81% | 96.56% | 1.44% |
| 13 | 99.17% | 99.31% | 99.40% | 99.64% | — | — |
| 26 | 98.64% | 98.62% | 96.52% | 91.06% | — | — |
| 39 | 99.64% | 94.18% | 88.99% | 79.05% | — | — |

KS = refrigerator temperature = 4–6° C.
RT = room temperature = 20–22° C.

The results of the stability examination clearly show that this formulation enables the protein rh-G-CSF to be stabilized over a longer time period in a partially amorphous vacuum-dried amino acid formulation provided the storage temperatures lie significantly below the glass transition temperatures (cf also comparative example C). Storage at 80° C. compared to storage at 60° C. shows this phenomenon relative to the glass transition at 77° C.

In order to additionally evaluate the products qualitatively SDS gel electrophoresis with silver staining was carried out for each determination of content. The results of this SDS gel electrophoresis are shown in example 8b. The same formulation was also stored for one year at various temperatures. The result is shown in Table 20a.

| | Water content [%] | Tg [° C.] | Monomer content G-CSF [%] |
|---|---|---|---|
| Start | 0.77 | 82.1 | 99.82 |
| After 52 weeks: | | | |
| KS | 1.20 | 79.52 | 98.34 |
| RT | 2.08 | 69.47 | 94.81 |
| 30° | 2.21 | 67.91 | 94.70 |
| 40° | 2.32 | 67.36 | 91.27 |
| 50° | 2.40 | 68.63 | 86.26 |

KS = refrigerator temperature = 4–6° C.
RT = room temperature = 20–22° C.

The experiment shows that it is possible to stabilize rh-G-CSF in a vacuum-dried partially amorphous L-arginine-L-phenylalanine formulation below the glass transition temperature.

COMPARATIVE EXAMPLE F rh-G-CSF in a Vacuum-dried L-arginine Formulation Containing Phosphoric Acid A solution containing 40 mg L-arginine, 0.1 mg polysorbate 80 and 0.35 mg rh-G-CSF per ml was prepared. After the pH value had been adjusted to pH 7.4 with phosphoric acid, the solution was treated, dried and analysed as described in example 8. The dried final product had a residual water content of 3.59% and a glass transition temperature of 8.6° C. This product was therefore present as a highly viscous, viscoplastic mass and not as a brittle amorphous glass after the drying was completed at room temperature. Stability of rh-G-CSF in a vacuum-dried L-arginine formulation.

TABLE 21

The amounts of monomer obtained in the HP-SEC are stated in %

| Storage period [weeks] | Storage temperatures | | | | | | |
|---|---|---|---|---|---|---|---|
| | −20° C. | KS | RT | 30° C. | 40° C. | 60° C. | 80° C. |
| 0 | — | — | 99.60% | — | — | — | — |
| 4 | 99.57% | 99.60% | 99.37% | 99.34% | 99.20% | 89.46% | 31.81% |
| 13 | 99.75% | 98.17% | 98.06% | 97.31% | 93.41% | — | — |
| 33 | 99.28% | 99.30% | 99.21% | 97.86% | 93.02% | — | — |

One does not achieve the same stabilizing effect that is obtained in a dry partially amorphous glass (example 8 and 17). This shows the importance of skilfully mixing the auxiliary substances in order to improve their drying properties during vacuum drying and thus obtain partially amorphous glasses at room temperature. This is particularly apparent at higher temperatures (30° and 40° C.). The stability is increased in this material compared to the vacuum-dried active substance without auxiliary substances (see comparative example D). In order to additionally evaluate the products qualitatively an SDS gel electrophoresis with silver staining was carried out for each determination of content. The results of this SDS gel electrophoresis are shown in example 8b.

COMPARATIVE EXAMPLE G rh-G-CSF Vacuum-dried in a Crystalline L-valine Glycine Formulation 0.35 mg rh-G-CSF per ml was added to a solution which contained 20 mg of L-valine and glycine and 0.1 mg polysorbate 80 per ml and whose pH value was adjusted to pH 7.4 with sodium hydroxide solution. The finished solution was treated, dried and analysed as described in example 8. The examination after the end of drying shows that the finished samples were a crystalline product having a residual water content of 0.82%. Stability of rh-G-CSF in a vacuum-dried crystalline L-valine-glycine formulation.

TABLE 22

The amounts of monomer obtained in the HP-SEC are stated in %

| Storage period [weeks] | \multicolumn{6}{c}{Storage temperatures} |||||| 
|---|---|---|---|---|---|---|
| | KS | RT | 30° C. | 40° C. | 60° C. | 80° C. |
| 0 | — | 94.36% | — | — | — | — |
| 4 | 89.93% | 89.66% | 84.26% | 72.47% | 44.54% | 27.44% |
| 13 | 74.14% | 73.91% | 64.90% | 46.82% | — | — |
| 33 | 73.75% | 70.04% | 54.93% | 40.40% | — | — |

KS = refrigerator temperature = 4–6° C.
RT = room temperature = 20–22° C.

This result clearly shows that a crystalline amino acid formulation is not able to stabilize rh-G-CSF even at low residual water contents. The destabilizing effect of such a formulation is clearly shown when compared with the vacuum-dried rh-G-CSF without auxiliary substances (see comparative example D).

In order to be able to evaluate the products qualitatively SDS gel electrophoresis with silver staining was additionally carried out for each determination of content. The results of this SDS gel electrophoresis are shown in example 8b.

EXAMPLE 10

Vacuum Drying of Erythropoietin in a Sucrose Formulation Containing L-arginine and L-phenylalanine A solution containing 50 mg sucrose, 10 mg of L-arginine and L-phenylalanine and 0.1 mg polysorbate 20 per ml was prepared. 5000 U erythropoietin (EPO) per ml were added to this solution and the pH value was adjusted to pH 7.2 with phosphoric acid. The solution was treated and dried as described in example 8. A dry partially amorphous product resulted having a residual water content of 0.56% and a glass transition temperature of 86.6° C. In the case of EPO the proportion of dimers that have formed in the manufactured product is a good criterium for the assessment of the stability of the product. The amounts of monomers and dimers determined by means of exclusion chromatography (3 single measurements per condition) are therefore a measure for the stabilizing effect of our preparations prepared by drying.

In exclusion chromatography protein molecules are separated in a dissolved state on the basis of their particle size i.e. high molecular components (dimers) are separated from EPO monomers. The examination (HP-SEC) was carried out on a HPLC system from Shimadzu using an autosampler (Gilson Abimed 231). A TSK gel G3000 SWXL (7.8×300 mm) column from the TosoHaas Co. was used as a separation column. The separated components were detected photometrically at 280 nm (Merck fluorescence spectrophotometer 820 FP). A 0.41 m sodium-potassium phosphate buffer containing sodium chloride pH 7.3 was used as the mobile solvent applied at a flow rate of 0.6 ml/min at room temperature. The samples to be examined were dissolved with redistilled water in such a way that the initial concentration was prepared again (addition of 1 ml). These dissolved samples were then stored in the autosampler until the examination. The injected amount of sample was 100 µl (=2 µg EPO), the run time of a sample was 25 min. The results were evaluated using an EPO working standard.

Stability of EPO in a vacuum-dried sucrose formulation containing L-arginine and L-phenylalanine.

TABLE 23

The amounts of monomer obtained in the HP-SEC are stated in %

| Storage period [weeks] | \multicolumn{3}{c}{Storage temperature} ||| 
|---|---|---|---|
| | KS | RT | 40° C. |
| 0 | — | 100% | — |
| 4 | 100% | 100% | 100% |
| 9 | 100% | 100% | 100% |
| 13 | 100% | 100% | 100% |
| 26 | 100% | 100% | 99.9% |

KS = refrigerator temperature = 4–6° C.
RT = room temperature = 20–22° C.

The result shows that it is possible to stabilize EPO by vacuum drying using the auxiliary substance combination selected in this case. In order to additionally qualitatively evaluate the products SDS gel electrophoresis with silver staining was carried out for each determination of content. The gel preparation, electrophoresis procedure and staining the gels were carried out as described in example 8 b. The samples were prepared in such a way that one mixed sample was prepared from 3 injection bottles. Subsequently this sample solution was diluted with sample buffer containing bromophenol blue resulting in an EPO concentration of 20 µg/ml. The samples were denatured for 5 minutes at 95° C. in a preheated heating block. A "Bio-Rad Standard Low" was used as the calibration proteins. This was prepared and treated exactly as the EPO samples. In addition an EPO working standard was prepared which was used as a comparison. The gel electrophoresis was carried out by means of a Midget gel electrophoresis unit (Pharmacia LKB 2050) and an accompanying voltage instrument. After it had been filled with electrophoresis buffer, 20 µl sample (i.e. 400 ng EPO) was filled into each gel pocket. The gels were observed visually after the staining was complete and the gels were photographed. Using this sensitive method it was possible to visualize very well the degradation and aggregation products of the monomer which were present in amounts >1%.

Result of the Electrophoresis

In the formulation described here only one monomer band corresponding to the working standard was detected in the gel in all the samples after 9 weeks. This emphasizes the stability of the protein in this formulation.

COMPARATIVE EXAMPLE H

Vacuum Drying Erythropoietin without Addition of Auxiliary Substances

In this experiment a starting solution was prepared which only contained the active substance EPO (50000 U/ml) in a dilute phosphate buffer (ca. 5 mM). The solution was prepared, treated and dried as described in example 8.

In this formulation is was not possible for technical reasons to determine the residual water content and the glass transition temperature of the final products since the amounts present in the vial were too low (ca. 0.2 mg). The stability of the protein was evaluated by means of exclusion chromatography as described in example 10.

Stability of EPO vacuum-dried without auxiliary substances

TABLE 24

The amounts of monomer obtained in the HP-SEC are stated in %

| Storage period [weeks] | Storage temperature | | |
|---|---|---|---|
| | KS | RT | 40° C. |
| 0 | — | 99.5% | — |
| 4 | 98.6% | 94.4% | 88.0% |
| 9 | 96.0% | 89.0% | 75.0% |
| 13 | 95.7% | 87.0% | 76.3% |
| 26 | 94.7% | 88.2% | 66.6% |

KS = refrigerator temperature = 4–6° C.
RT = room temperature = 20–22° C.

An SDS gel electrophoresis with silver staining was also carried out for each determination of content. Preparation of the gels, preparation of the samples, electrophoresis procedure and staining of the gels was carried out as described in example 10. After staining the gels it was possible to clearly detect a dimer band in all samples at each storage temperature in addition to the monomer band corresponding to the band of the working standard. This experiment clearly shows the stabilizing effect of the auxiliary substance combination used in example 10. The stability of the pure active substance in this example is clearly reduced compared to the stability of the active substance in the formulation of example 10; it is possible to observe the formation of diners. The higher the storage temperature the more significant is the protective effect of the selected combination of auxiliary substances in experiment 10.

EXAMPLE 11

Lactate Dehydrogenase Vacuum Dried in a Formulation Containing Maltose-L-arginine and L-phenylalanine A solution containing 50 mg maltose monohydrate, 10 mg L-arginine and 10 mg L-phenylalanine per ml was prepared. Lactate dehydrogenase (LDH) was added to this solution so that a protein activity of 165 U/ml resulted. The pH value of the solution was adjusted to pH 7.0 using phosphoric acid. The solution was prepared, treated and dried as described in example 8. After drying a homogeneous product with a glass transition temperature of 96° C. and a residual water content of 0.82% was present. The final samples were stored at various temperatures and the protein activity was evaluated after various storage periods. In the case of LDH the enzymatic activity was used as a measure of the protein stability. This determination was carried out photometrically. In a sample solution pyruvate and NADH are reduced to lactate and NAD by the catalytic action of LDH. The decrease in the NADH content in the solution can be monitored photometrically ($\lambda$=365 nm; $\epsilon$=3.4 cm$^2$/μmol). The activity was measured in 100-fold or 200-fold diluted starting solutions in a plastic cuvette (path length=1 cm) (Perkin Elmer 552 UV/VIS spectrophotometer). It was possible to calculate the protein activity of the LDH by the decrease per time unit. Stability of LDH in a vacuum-dried maltose formulation containing L-arginine and L-phenylalanine. The activity of the starting solution corresponded to a value of 100%.

TABLE 25

The activity is stated in % as obtained in the examination

| Storage period [weeks] | Storage temperature | | | | |
|---|---|---|---|---|---|
| | KS | RT | 30° C. | 40° C. | 50° C. |
| 0 | — | 85.3% | — | — | — |
| 5 | 87.81% | 87.45 | 81.15% | 80.42% | 64.42% |
| 13 | 83.28% | 79.41% | 78.79% | 61.74% | — |

KS = refrigerator temperature = 4–6° C.
RT = room temperature = 20–22° C.

The experiment clearly shows the stabilizing effect of the formulation for the very sensitive protein LDH.

COMPARATIVE EXAMPLE I

Vacuum Drying of Lactate Dehydrogenase without Addition of Auxiliary Substances In this experiment a solution of the pure active substance lactate dehydrogenase (LDH) with an activity of 136 U/ml was prepared in a dilute phosphate buffer (8 mM). The solution was prepared, treated and dried as described in example 8. In this formulation it was not possible for technical reasons to determine the residual water content and the glass transition temperature of the final products since the amounts present in the vial were too low (ca. 0.2 mg). The stability of the protein was evaluated as described in example 11. Stability of LDH vacuum-dried without auxiliary substances. The activity of the starting solution corresponded to a value of 100%.

TABLE 26

The activity is stated in % as obtained in the examination

| Storage period [weeks] | Storage temperature | | |
|---|---|---|---|
| | KS | RT | 40° C. |
| 0 | — | 64.52% | — |
| 5 | 66.54% | 23.03% | 1.57% |
| 13 | 50.63% | 6.81% | 0% |

KS = refrigerator temperature = 4–6° C.
RT = room temperature = 20–22° C.

This experiment clearly shows the stabilizing effect of the auxiliary substance combination used in example 11. The stability of the pure active substance in this example is considerably lower than the stability of the active substance in the formulation of example 11. The higher the storage temperature, the more significant is the protective effect of the selected combination of auxiliary substances in example 11. The difference between the stability of the pure protein and the protein dried in an auxiliary substance combination is most pronounced for LDH.

EXAMPLE 12

Lactate Dehydrogenase in a Sugar-free, Vacuum-dried L-arginine-L-phenylalanine Formulation A stock solution was prepared containing 20 ml L-arginine and 20 mg L-phenylalanine per ml. Lactate dehydrogenase (LDH) was added to this after adjusting the pH value to pH 7.0 with phosphoric acid so that a starting solution was obtained having a protein activity of 168 U/ml. The solution was prepared, treated and dried as described in example 8. After drying a homogeneous product was present with a glass transition temperature of 103.90° C. and a residual water content of 1.18%. The final samples were stored at various temperatures and the protein activity was evaluated at various storage periods. The protein analysis was carried out as described in example 11. Stability of LDH in a vacuum-dried sugar-free L-arginine-L-phenylalanine preparation. The activity of the starting solution before drying corresponded to a value of 100%.

TABLE 27

The enzyme activity is stated in % as obtained in the activity test

| Storage period | Storage temperature | | | | |
|---|---|---|---|---|---|
| [weeks] | KS | RT | 30° C. | 40° C. | 60° C. |
| 0 | — | 80.36% | — | — | — |
| 4 | 79.70% | 82.08% | 79.34% | 77.62% | 70.54% |
| 13 | 82.25% | 76.11% | 75.21% | 73.06% | — |

The experiment clearly shows the stabilizing effect of this amino acid formulation over the entire investigated temperature range. The stability of LDH is significantly increased compared to drying the pure active substance (comparative example I).

COMPARATIVE EXAMPLE J

Lactate Dehydrogenase in a Crystalline Vacuum-dried L-valine-glycine Formulation A stock solution was prepared containing 20 mg L-valine and 20 mg glycine per ml. Lactate dehydrogenase (LDH) was added to this after adjusting the pH value to pH 7.0 with an NaOH solution so that a starting solution with a protein activity of 147 U/ml resulted. The solution was prepared, treated and dried as described in example 8. After drying a homogeneous completely crystalline product was present with a residual water content of 1.12%. The final samples were stored at various temperatures and the protein activity was evaluated after various storage periods as described in example 11. Stability of LDH in a vacuum-dried completely crystalline L-valine-glycine formulation. The activity of the starting solution before drying corresponded to a value of 100%.

TABLE 28

The enzyme activity is stated in % as obtained in the activity test

| Storage period | Storage temperature | | | | |
|---|---|---|---|---|---|
| [weeks] | KS | RT | 30° C. | 40° C. | 60° C. |
| 0 | — | 9.26% | — | — | — |
| 5 | 3.69% | 2.11% | 1.09% | 0.80% | 0.0% |
| 13 | 0.08% | 0.01% | 0% | 0% | 0% |

This experiment clearly shows that a crystalline amino acid formulation has a very negative influence on the enzyme during the vacuum drying. 90% activity is already lost even during the drying which means during the formation of the crystalline supporting structure. Even when stored at various temperatures the activity that is still present cannot be maintained. After 5 weeks the initial values of the samples have deteriorated further. Thus a completely crystalline amino acid formulation is entirely unsuitable for stabilizing LDH.

EXAMPLE 13

A pure maltose solution (50 mg/ml) and a solution containing maltose and phenylalanine (40 mg/ml maltose and 10 mg/ml phenylalanine) were vacuum-dried in this experiment. In parallel to this similar preparations were prepared to which 10 µg/ml rh-ngf or 100 µg/ml PTH(1–37) or 500 µg/ml ularitide were added. The solutions were sterile filtered after the preparation and dispensed into 2 ml vials. The samples were vacuum-dried at 20° C. and samples were taken from both formulations after predetermined time periods. The residual filling amount, the water content according to Karl-Fischer and the Tg were determined in these samples. A plate temperature of 20° C. was maintained during the entire drying period. The pressure in the chamber was reduced stepwise to ca. $10^{-3}$ mbar. The filling weight of the vials decreases in both these formulations within 7 hours to about 6% of the initial value i.e. the solutions concentrate very rapidly. In the pure maltose formulation a supersaturated solution is initially formed which then changes into a rubber-like state. In the further course of the drying a slight advantage can be observed in the mass decrease of the formulation containing phenylalanine compared to the pure sugar solution. Ca. 5.5% of the original filling weight is still present in the vials when the drying of the maltose samples is completed whereas about 4.9% of the filling amount is still present in the vials with the maltose-phenylalanine mixture.

This result becomes even more pronounced when the change in the water content in the samples is observed instead of the change in the filling weight. At the beginning of the drying process the solution is composed to 95.08% of water i.e. ca. 965 mg water is contained in each vial. The aim is to achieve a dry product with a residual moisture content of 1–2%. With an amount of solids of 50 mg this 1–2% then corresponds to 0.5–1 mg water per bottle. Correspondingly ca. 99.95% of the water present has to sublime from the sample during drying in order to obtain a dry product. In an advanced stage of the drying the water content of the samples was determined according to Karl Fischer. This was carried out for the samples containing phenylalanine by directly introducing the samples into the methanol solution. The very sticky sugar cannot be directly transferred to the methanol solution. This was firstly dissolved in anhydrous DMF. Then the water content of this solution was determined. FIG. 3a shows the results of the residual water determination carried out in this way. The advantage of the preparation containing amino acids can clearly be seen. The residual water content has already declined to 2.7% after only 17 hours drying whereas it is still at 13.59% in the maltose formulation. This result shows the advantage of the solution containing phenylalanine. It is not possible to dry maltose under these process conditions within 48 hours. After the drying is complete a "rubber" with a considerable residual water content is still present at RT. The glass transition temperatures of the individual samples were determined by means of DSC in addition to the residual water contents. Since the glass transition temperatures directly correspond to the water content of the samples, the mixture containing maltose-phenylalanine exhibits significantly increased values. The result shows that the Tg of the amino acid-sugar mixtures is already in the range of the plate temperature after ca. 10 hours. The corresponding measured values are shown in FIG. 3b. Since at this stage in the drying process very little water still evaporates, the product temperature is also in the range of the plate temperature. Thus a glass is already present at room temperature in the vials after 10 hours of the drying process. In the case of stabilizing the proteins with such a formulation this means that the protein is already embedded in a stabilizing glass after 10 hours. The time period in which the protein is present in a concentrated solution or in a "rubber-like" form is therefore very short which is of great advantage for the stability of the active substance. In contrast the pure sugar is still present as a "rubber" after the drying is completed at room temperature and thus has no stabilizing effect on the active substance in the case of a product containing protein.

The various preparations containing protein do not differ in their other physical parameters from those of the basic formulations free of active substance.

The invention claimed is:

1. A process for producing a dry erythropoietin composition in at least partially amorphous form comprising:
   (a) providing a solution containing erythropoietin or fragment thereof; at least one sugar; a polar amino acid selected from the group consisting of arginine, aspartic acid, glutamic acid, histidine, citrulline, lysine and ornithine; and an apolar amino acid selected from the group consisting of phenylalanine, tryptophan, leucine, methionine, valine, alanine, glycine, acetylphenylalanine ethyl ester, cysteine, sarcosine and isoleucine; and
   (b) vacuum drying said solution without freezing to produce said dry erythropoietin composition.

2. A dry composition, comprising erythropoietin or fragment thereof; at least one sugar; a polar amino acid selected from the group consisting of arginine, aspartic acid, glutamic acid, histidine, citrulline, lysine and ornithine; and an apolar amino acid selected from the group consisting of phenylalanine, tryptophan, leucine, methionine, valine, alanine, glycine, acetylphenylalanine ethyl ester, cysteine, sarcosine and isoleucine; wherein said protein or fragment thereof is in at least partially amorphous form, with the proviso that the dry composition is vacuum-dried.

3. A method of drying a solution of erythropoietin or fragment thereof to produce a dry composition, comprising: forming a solution of said erythropoietin or fragment thereof which further comprises at least one sugar, a polar amino acid selected from the group consisting of arginine, aspartic acid, glutamic acid, histidine, citrulline, lysine and ornithine, and an apolar amino acid selected from the group consisting of phenylalanine, tryptophan, leucine, methionine, valine, alanine, glycine, acetylphenylalanine ethyl ester, cysteine, sarcosine and isoleucine; and vacuum drying said solution without freezing to produce a dry composition.

4. The process of claim 1, wherein said sugar is sucrose.

5. The process of claim 1, wherein said vacuum drying is carried out as a continuous drying process.

6. The process of claim 1, wherein the dry composition has an increased glass transition temperature compared to a dry composition without an apolar amino acid.

7. The process of claim 1, wherein said dry composition is dried in single dose containers.

8. The process of claim 1, further comprising grinding the dry composition to form a powder.

9. A dry composition produced by the process of claim 1.

10. The dry composition of claim 9, wherein the composition has a glass transition temperature above 4° C. and a residual moisture content of less than 6% (g/g).

11. The dry composition of claim 2, wherein the composition has a glass transition temperature above 4° C. and a residual moisture content of less than 6% (g/g).

12. The dry composition of claim 10, wherein the glass transition temperature is above 20° C.

13. The dry composition of claim 11, wherein the glass transition temperature is above 20° C.

14. The dry composition of claim 10, wherein the residual moisture content is less than 4% (g/g).

15. The dry composition of claim 11, wherein the residual moisture content is less than 4% (g/g).

16. The dry composition of claim 9, wherein said composition has at least 10% higher apparent density than a corresponding lyophilisate.

17. The dry composition of claim 2, wherein said composition has at least 10% higher apparent density than a corresponding lyophilisate.

18. The dry composition of claim 9, wherein said protein or fragment thereof remains in at least partially amorphous form upon storage for a period of at least two weeks.

19. The dry composition of claim 2, wherein said protein or fragment thereof remains in at least partially amorphous form upon storage for a period of at least two weeks.

20. The dry composition of claim 9, wherein said erythropoietin or fragment thereof is a therapeutically active agent.

21. The dry composition of claim 2, wherein said erythropoietin or fragment thereof is a therapeutically active agent.

22. The process of claim 1, wherein the solution contains both a carbohydrate and a polar zwitterionic compound.

23. A method of claim 1, wherein said vacuum drying is carried out in a freeze-drying apparatus, without freezing.

24. The dry composition of claim 18 wherein said protein or fragment thereof remains in at least partially amorphous form upon storage for a period of at least twenty-six weeks.

25. The dry composition of claim 19 wherein said protein or fragment thereof remains in at least partially amorphous form upon storage for a period of at least twenty-six weeks.

* * * * *